United States Patent

Wang et al.

[11] Patent Number: 6,090,472
[45] Date of Patent: *Jul. 18, 2000

[54] NONWOVEN, POROUS FABRIC PRODUCED FROM POLYMER COMPOSITE MATERIALS

[75] Inventors: James H. Wang, Appleton, Wis.; David M. Schertz, Roswell, Ga.

[73] Assignee: Kimberly-Clark Worldwide, Inc., Neenah, Wis.

[*] Notice: This patent issued on a continued prosecution application filed under 37 CFR 1.53(d), and is subject to the twenty year patent term provisions of 35 U.S.C. 154(a)(2).

[21] Appl. No.: 09/001,791

[22] Filed: Dec. 31, 1997

[51] Int. Cl.[7] ............................................. B32B 5/24
[52] U.S. Cl. ........................... 428/198; 442/366; 442/409
[58] Field of Search ................. 428/198, 43, 286, 428/290, 350, 172; 442/366, 409

[56] References Cited

U.S. PATENT DOCUMENTS

| | | |
|---|---|---|
| 2,185,789 | 1/1940 | Jacqué . |
| 3,097,991 | 7/1963 | Miller et al. . |
| 3,121,040 | 2/1964 | Shaw et al. ............................. 161/177 |
| 3,323,978 | 6/1967 | Rasmussen . |
| 3,417,064 | 12/1968 | Bailey ..................................... 260/79.5 |
| 3,435,705 | 4/1969 | Harmon . |
| 3,461,193 | 8/1969 | Gilardi . |
| 3,515,325 | 6/1970 | Kalwaites . |
| 3,539,666 | 11/1970 | Schirmer . |
| 3,546,716 | 12/1970 | Laumann ..................................... 4/112 |
| 3,564,677 | 2/1971 | Kalwaites . |
| 3,577,586 | 5/1971 | Kalwaites et al. . |
| 3,595,454 | 7/1971 | Kalwaites . |
| 3,639,199 | 2/1972 | Brandts et al. . |
| 3,656,672 | 4/1972 | Kalwaites . |
| 3,675,391 | 7/1972 | Gallacher . |
| 3,712,847 | 1/1973 | Rasmussen . |
| 3,717,541 | 2/1973 | Schirmer . |
| 3,719,540 | 3/1973 | Hall . |
| 3,783,093 | 3/1974 | Gallacher . |
| 3,783,872 | 1/1974 | King ........................................ 128/284 |

(List continued on next page.)

FOREIGN PATENT DOCUMENTS

| | | |
|---|---|---|
| 0 436 966 A2 | 8/1967 | European Pat. Off. . |
| 1199566 | 8/1967 | United Kingdom . |
| WO 98/29508 | 7/1998 | WIPO . |

OTHER PUBLICATIONS

"Microfiber Formation: Immiscible Polymer Blends Involving Thermoplastic Poly(vinyl alcohol) as an Extractable Matrix," by L.M. Robeson, R. J. Axelrod, M. S. Vratsanos, & M. R. Kittek, *Journal of Applied Polymer Science*, pp. 1837–1846, vol. 52, 1994, John Wiley & Sons, Inc.

"Process for Making Smooth Vapor–Permeable Microporous Sheet Material", by T.S. Govindan, *Defensive Publication*, T901,007, Aug. 1, 1972.

*Primary Examiner*—Marion McCamish
*Assistant Examiner*—Arti Singh
*Attorney, Agent, or Firm*—Jones & Askew, LLP

[57] ABSTRACT

A nonwoven, porous fabric produced from a water modifiable polyolefin-containing film. In a preferred embodiment, the nonwoven fabric includes groups of elongated polyolefin fibers substantially oriented along a longitudinal axis. The fibers have branches extending from themselves and are bonded therebetween. Elongated channels extend generally parallel to the longitudinal axis on the surface of the fabric and within the fabric. A substantial portion of the channels are interconnected to other channels. To produce the fabric, a polymer blend is formed with the polyethylene as the minority constituent and the dispersed phase, and with polyethylene oxide as the continuous phase. In another embodiment wherein the polyethylene is the majority constituent and the polyethylene oxide is the minority constituent, a reactive blend is prepared during processing so that the blend exhibits an inverse phase morphology, the polyethylene oxide becoming the continuous phase and the polyethylene becoming the dispersed phase. In either embodiment, the blend is extruded into a film, which is then treated with an aqueous solvent to remove the polyethylene oxide to produce the nonwoven, porous fabric. The resulting nonwoven, porous fabric has a silk-like hand and shine ideal for disposable personal hygiene articles, and is flushable through waste water disposal systems.

25 Claims, 7 Drawing Sheets

U.S. PATENT DOCUMENTS

| | | |
|---|---|---|
| 3,796,778 | 3/1974 | Gallacher . |
| 3,954,928 | 5/1976 | Omori et al. . |
| 3,991,754 | 11/1976 | Gertzman . |
| 4,105,033 | 8/1978 | Chatterjee et al. ............... 128/285 |
| 4,141,713 | 2/1979 | Ammannati et al. . |
| 4,301,203 | 11/1981 | Keuchel . |
| 4,344,804 | 8/1982 | Bijen et al. . |
| 4,372,311 | 2/1983 | Potts ............... 128/287 |
| 4,377,544 | 3/1983 | Rasmussen . |
| 4,837,078 | 6/1989 | Harrington . |
| 5,033,172 | 7/1991 | Harrington . |
| 5,045,387 | 9/1991 | Schmalz . |
| 5,096,640 | 3/1992 | Brody et al. . |
| 5,102,601 | 4/1992 | Farris et al. . |
| 5,104,367 | 4/1992 | Hill . |
| 5,120,598 | 6/1992 | Robeson et al. . |
| 5,178,812 | 1/1993 | Sanford et al. . |
| 5,182,162 | 1/1993 | Andrusko . |
| 5,190,533 | 3/1993 | Blackburn ............... 604/367 |
| 5,192,606 | 3/1993 | Proxmire et al. ............... 428/284 |
| 5,196,247 | 3/1993 | Wu et al. ............... 428/43 |
| 5,200,248 | 4/1993 | Thompson et al. ............... 428/131 |
| 5,205,968 | 4/1993 | Damrow et al. . |
| 5,208,098 | 5/1993 | Stover . |
| 5,227,101 | 7/1993 | Mahoney et al. . |
| 5,246,647 | 9/1993 | Beck et al. . |
| 5,248,461 | 9/1993 | Pluyter et al. . |
| 5,257,982 | 11/1993 | Cohen et al. . |
| 5,300,358 | 4/1994 | Evers ............... 428/286 |
| 5,330,827 | 7/1994 | Hansen . |
| 5,470,640 | 11/1995 | Modrak . |
| 5,508,101 | 4/1996 | Patnode et al. ............... 428/286 |
| 5,547,746 | 8/1996 | Burton, Sr. ............... 428/288 |
| 5,567,510 | 10/1996 | Patnode et al. ............... 428/288 |
| 5,658,268 | 8/1997 | Johns et al. ............... 604/361 |
| 5,700,872 | 12/1997 | Wang et al. . |
| 5,763,065 | 6/1998 | Patnode et al. ............... 428/219 |

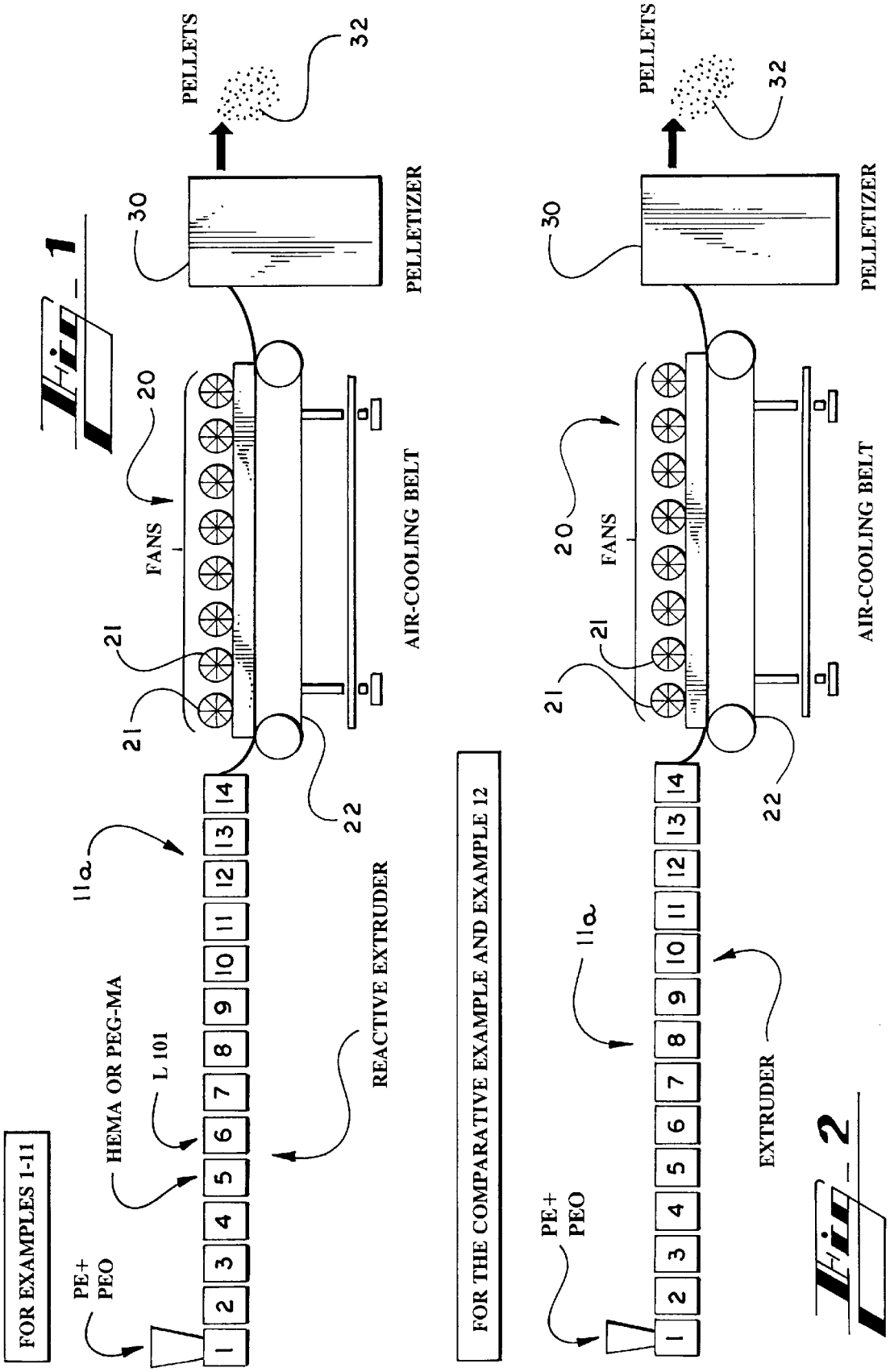

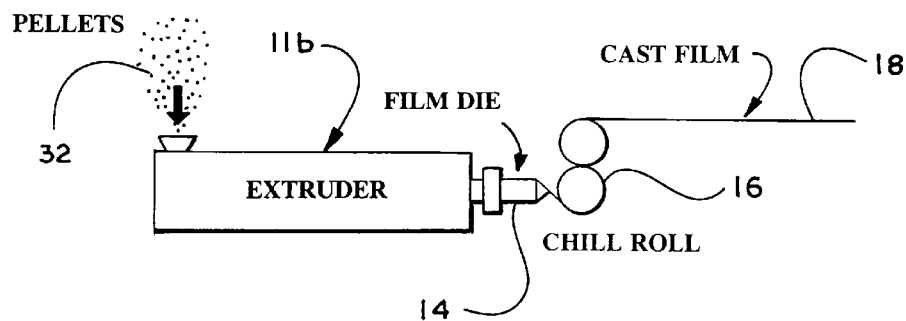
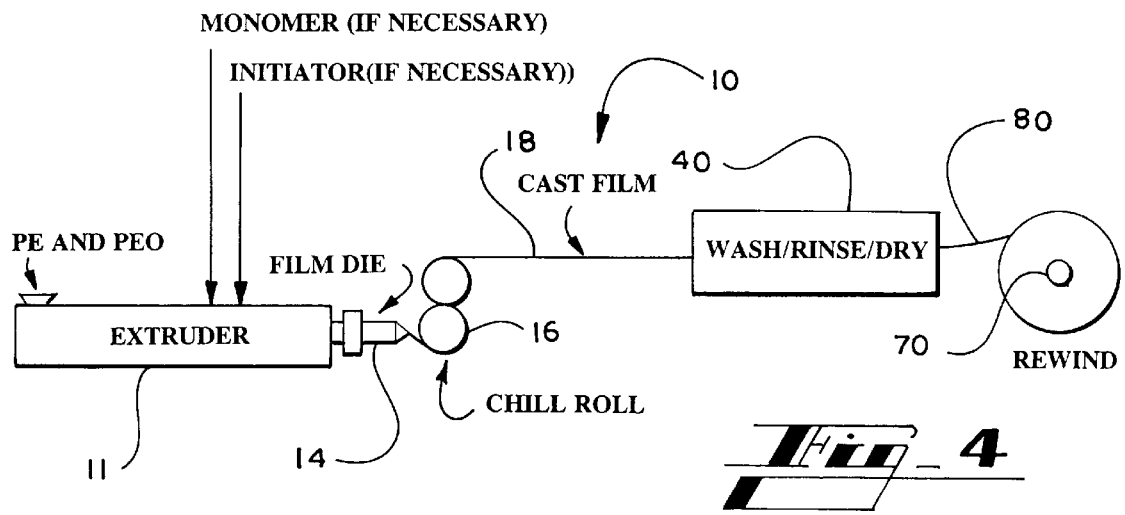
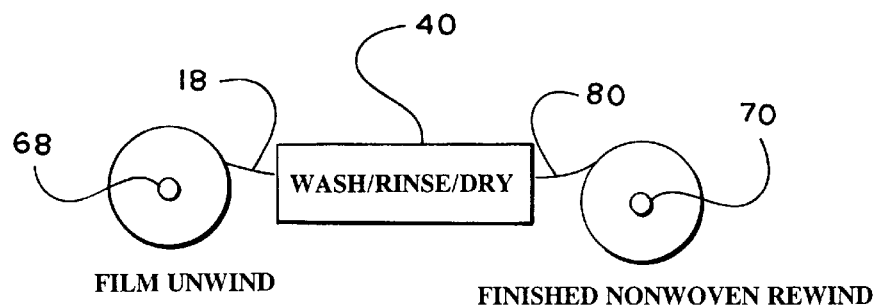

NONWOVEN, POROUS FABRIC PRODUCED FROM POLYMER COMPOSITE MATERIALS

BACKGROUND OF THE INVENTION

1. Field of the Invention

The present invention relates to a nonwoven, porous fabric made from polymer composite materials useful in disposable personal hygiene articles. This invention more particularly pertains to a porous, wettable fabric having directionally oriented, elongated fibers and interconnected, elongated channels.

2. Description of the Background Art

Disposable personal care products such as diapers, tampons, pantiliners etc. are a great convenience. Such products conveniently provide the benefit of one time, sanitary use and are quick and easy to use. However, disposal of such products is a concern because of depleted landfill space and the undesirability of incineration. Moreover, the difficulty and costs associated with separating such products in preparation of disposal is also of concern. Consequently, there is a need for a porous, wettable, nonwoven fabric which can maintain its intended structure during personal use, but which is entirely acceptable in conventional sewage systems. Personal care products which are flushable in conventional sewage systems provide the benefit of convenient, cost effective and conscientious disposal.

Presently, commercially available fabrics of composite polymers, produced with the use of extrusion devices, are often woven after the polymer composition is forced through the fine holes of a spinneret to form continuous filaments of the man-made fiber. The subsequent drafting and twisting together of the fibers to form the yarn is called spinning. Moreover, various methods of spinning are known such as melt spinning, solution spinning and flash spinning. To make fabric, the fibers are twisted together to make a strand of yarn and, typically, the strands of spun yarn are then woven together.

There are commercially available fabrics of composite polymers which are not woven. These known nonwoven fabrics are produced from processes which are equally known. For example, one of these nonwoven fabrics is know as a spunbond fabric. A spunbond fabric uses a spinneret to form fibers which fall down into an air gun. The fibers are sprayed with air so that the continuous fibers are randomly laid upon one another. The entangled, continuous fibers are then wound onto a forming wire. Since the fibers are not woven, bonding is necessary to allow the entangled fibers to maintain their desired form. Adhesive or heating is often used to bond the entangled fibers to form the fabric.

A second type of nonwoven fabric is meltblown fabric. In this example, the fibers are extruded from a spinneret as with spunbonding, but they are very fine. A fast stream of air is blown into the melt as it exits from the holes of the spinneret. The air draws the melt to produce microfibers typically 3 to 5 microns in diameter. The web is collected on a forming wire. The fibers are hot when they fall into the mass and form some bonding, but normally an additional thermal or adhesive bonding step is performed.

Another example of a nonwoven fabric is air laid fabric which is also produced from a known process. An air laid nonwoven fabric is produced from small, lint-like fibers dropped in the air. A vacuum draws the fibers down to make a random collection of fibers which may also be adhesively or thermally bonded.

The nonwoven fabrics produced from these known processes may be characterized by their fiber lengths, orientation, and the resulting channels or capillaries between the fibers produced by the bonds between the fibers. In the case of nonwoven fabrics designed for fluid management and distribution, the channels provide a place for water to go. Both elongated fibers and channels are desired in order to obtain optimal fluid intake and wicking along with a strong fabric. The spunbond fabrics include long, continuous fibers which form short channels therebetween. In the case of melt blown fabrics, both the fibers and the channels are short. The air laid fabrics have short fibers but moderately lengthened channels. In any case, the optimal configuration of long, continuous fibers with long channels does not exist in any known nonwoven fabric and, moreover, may not be produced by any known process. Therefore, the desired strength as a result of the structural integrity of bonded continuous fibers in conjunction with the increased water intake and wicking obtained from elongated channels does not exist in these known nonwoven fabrics. In short, a disadvantage associated with the typical nonwoven fabrics is that the fibers are not directionally oriented or the channels are obstructed by bonds between the fibers. The nonwovens, in and of themselves, are not wettable unless they are treated or coated with surfactants. However, these surfactants are not permanent on the nonwoven fabrics.

There are some patents known to disclose the processing of polymeric compositions with preparation of a polymer blend by specifically dissolving one polymer component in another. For example, U.S. Pat. No. 3,539,666 to Schirmir discloses a method for producing a nonwoven fabric-like member. A thermoplastic composition comprising a blend of different polymers is extruded through an annular die to form a seamless cellular tube which is biaxially stretched by drawing over a mandrel. A substantial portion of the individual cells in the tube rupture to form a porous web-like structure resembling a nonwoven fabric. Once cooled, the resultant structure may be drawn off the mandrel and slit to form a sheet.

U.S. Pat. No. 5,178,812 to Sanford et al. discloses a method of making composites having improved surface properties. In Sanford, a polymer matrix is extracted from the interior of a composite material in order to increase the matrix concentration at the material's surface. Before selectively dissolving the polymer matrix with an acidic solvent, the fibers may be formed by spinning, extruding a dope into films or fibridating the dope into fibrids. The process in Sanford then involves treating the material with a solvent which dissolves the polymer matrix while not substantially dissolving the reinforcing polymer phase. Next, the solvent is removed whereby at least some of the polymer matrix is extracted from the interior of the material and the matrix concentration increases at the material's surface. In short, Sanford simply teaches a process for improving surface properties such as adhesiveness in a composite construction. Sanford does not disclose a nonwoven fabric as does the present invention.

U.S. Pat. No. 5,096,640 to Brody et al. discloses a method of producing a highly porous, melt spun, fibrous tube for use as a separation medium. In Brody, a blend of polymer components are placed in a solvent. One of the two components is then leached out to produce a tube having a wall consisting of interpenetrating networks of two polymeric components. One of the two components in the interpenetrating network leaches out to produce the tube. Brody requires the blend to be spinnable. Moreover, Brody neither teaches a simple blend nor a permanently wettable fabric as does the present invention.

U.S. Pat. No. 5,227,101 to Mahoney et al. teaches preparation of a porous membrane from a polymer blend by dissolving one component of the blend. In Mahoney, the invention relates to a process for making microporous membranes for liquid or gas separations by mixing a poly (etheretherketone)-type polymer and a low melting point crystallizable polymer. A plasticizer dissolves at least 10 weight percent of the poly(etheretherketone)-type polymer that is present at the membrane fabrication temperature. The plasticizer may be made of a solvent such that at least 10 weight percent of the poly(etheretherketone)-type polymer is dissolved. Mahoney discloses extruding polymeric mixtures into membranes and then immersing the membrane in a leach bath. In Mahoney, the mixture of polymers and plasticizer is extruded through a spinneret. The invention in Mahoney focuses on the manufacture of filtration and/or separation membranes. However, a nonwoven fabric as in the present invention is not disclosed.

U.S. Pat. No. 3,323,978 to Rasmussen also discloses processing of polymeric composition to form textile fibers. Rasmussen teaches a two-phase fibrous microstructure comprising of a distinctly hydrophobic component and a distinctly hydrophilic component. The fibers are produced from a film material which is treated with a swelling agent for the distinctly hydrophilic component. The swelled product is subsequently split into individual fibers or a coherent network of fibers. By swelling, the material of the hydrophilic fibrils is weakened. The surfaces resulting from the splitting will mainly be the in the hydrophilic substance so that the fibers will have an accumulation of hydrophilic substance at the surfaces which is what Rasmussen discloses as desirable. Rasmussen also does not teach a nonwoven, porous fabric as does the present invention.

Although nonwoven fabrics are known in the art, these known fabrics are inadequate or outright impractical. Earlier nonwoven fabrics typically have blended fiber components that result in a fabric having a heterogeneous surface structure. The fibers of these known fabrics are substantially unoriented. Moreover, as previously mentioned herein, the fibers and channels of these known fabrics are not as elongated as the fabric of present invention and the channels are not interconnected to the extent the fabric of the present invention is. Channels are typically blocked by the bonding points between the fibers in these known fabrics which impedes fluid flow therethrough. Therefore, these known fabrics are not permanently wettable as is the product of the present invention. The fabric of the present invention has a great variety of surface structure and directional fiber distribution.

However, fibers formed from higher molecular weights such as film grade polyethylene cannot easily be formed into fibers even deliberately by the known, conventional spinning processes. For example, melt spinning difficulties arise from the extremely high melt viscosity of the high molecular weight resin at the shear rate typically encountered in melt spinning processes such as melt blown and spunbond processes. Further, the high molecular weight polyethylene has inherently high melt strength and low melt drawability which makes the aerodynamic drawing very difficult.

Thus, despite the attempts described above to produce nonwoven fabrics and to form materials from polymer blends, no method has been developed to produce a polyolefin fabric that is wettable and that can be accepted as flushable through conventional waste water disposal systems.

Due to its unique interaction with water and body fluids, polyethylene oxide (hereinafter PEO) may be utilized as a component material for flushable products. PEO,

is a commercially available water-soluble polymer that can be produced from the ring opening polymerization of the ethylene oxide,

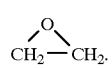

Because of its water-soluble properties, PEO is desirable for flushable applications. However, there is a dilemma in utilizing PEO in the flushable applications.

Low molecular weight PEO resins have desirable melt viscosity and melt pressure properties for extrusion processing but have limitations when melt processed into structural articles such as thin films. An example of a low molecular weight PEO resin is POLYOX® WSR N-80 which is commercially available form Union Carbide. POLYOX® WSR N-80 has an average approximate molecular weight of 200,000 g/mol as determined by melt rheology measurements. As used herein, low molecular weight PEO compositions are defined as PEO compositions with an average molecular weight of less than and including approximately 200,000 g/mol.

In the personal care industry, thin-gauged films are desired for commercial viability and ease of disposal. The low melt strength and low melt elasticity of low molecular weight PEO limit the ability of the low molecular weight PEO to be drawn into films having a thickness of less than about 2 mil. Although low molecular weight PEO can be thermally processed into films, thin-gauged films of less than about 1 mil in thickness cannot be obtained due to the lack of melt strength and melt elasticity of the low molecular weight PEO. The processability of PEO may be improved by blending the PEO with a second polymer, a copolymer of ethylene and acrylic acid, in order to increase the melt strength. The PEO/ethylene acrylic acid copolymer blend may be processed into films of about 1.2 mils in thickness. However, the blend and resulting film are not water-soluble. More importantly, thin films made from low molecular weight PEO are too weak and brittle to be useful for personal care applications. Low molecular weight PEO films have low tensile strength, low ductility, and are too brittle for commercial use. Further, films produced from low molecular weight PEO and blends containing low molecular weight PEO become brittle during storage at ambient conditions. Such films shatter and are not suited for commercial applications.

High molecular weight PEO resins are expected to produce films with improved mechanical properties compared to films produced from low molecular weight PEO. An example of a high molecular weight PEO is POLYOX® WSR 12K which is commercially available from Union Carbide. POLYOX® WSR 12K has an average approximate molecular weight of 1,000,000 g/mol as determined by melt rheology measurements. As used herein, high molecular weight PEO compositions are defined as PEO compositions with an average molecular weight of greater than and including approximately 300,000 g/mol.

High molecular weight PEO has poor processability due to its high melt viscosity and poor melt drawability. Melt pressure and melt temperature are significantly elevated during melt extrusion of high molecular weight PEO. During extrusion of high molecular weight PEO, severe melt fracture is observed. Only very thick sheets can be made from high molecular weight PEO. High molecular weight PEO cannot be thermally processed into films of less than about 7 mil in thickness. High molecular weight PEO suffers from severe melt degradation during extrusion processes. This results in breakdown of the PEO molecules and formation of bubbles in the extrudate. The inherent deficiencies of high molecular weight PEO makes it impossible to utilize high molecular weight PEO in film applications. Even the addition of high levels of plasticizer to the high molecular weight PEO do not improve the melt processability of high molecular weight PEO sufficiently to allow the production of thin films without melt fracture and film breakage occurring.

Currently available nonwoven, porous fabrics are not practical for personal care applications. Thus, there has been a need in the art for a nonwoven polyolefin fabric that is produced without spinning or drawing from polymer components of varying molecular weight, is strong enough for extended personal use, has enhanced fluid intake and wicking, may be permanently wettable, and is entirely flushable down conventional sewage systems.

SUMMARY OF THE INVENTION

The invention seeks to provide a nonwoven, fabric of the above-mentioned kind which has a silk-like hand and shine, is permanently wettable, and can be utilized in articles such as personal care products that are capable of being entirely disposed in conventional sewage systems.

In accordance with the invention, this object is accomplished by providing a nonwoven fabric comprising at least one group of elongated fibers of the polyolefin substantially oriented along a longitudinal axis, a plurality of branches of the fibers extending across multiple fibers in the fabric, thermal bonds formed between adjacent fibers and between the branches and fibers crossed by the branches, and elongated channels extending generally parallel to the longitudinal axis on the surface of the fabric and within the fabric. A substantial proportion of the channels are interconnected to other channels and are therefore continuous such that the fabric of the present invention has significantly greater fluid intake and wicking than other known fabrics.

The fabric of the present invention may be made using a method for extruding a polymer blend, formed from a soluble component and a non-soluble component to form a film, and processing the film to produce the nonwoven fabric. The non-soluble component must be the dispersed phase in the blend, regardless of whether it is the majority or minority constituent of the blend. After extruding the polymer blend into a film, the film is washed to remove the soluble polymer component and to reveal the nonwoven web. The non-soluble polymer does not significantly dissolve. The non-soluble polymer preferably is a polyolefin, such as polyethylene (PE). The soluble polymer preferably is polyethylene oxide (PEO). In a preferred process, the components are blended in a manner that results in the fabric being porous. It is also possible to make the fabric wettable by utilizing a reactive blend of the components. This novel process eliminates the spinning and drawing processes typically associated with extrusion of polymer compositions. The non-soluble polymer component of the blend (such as PE) must be the dispersed phase. This allows an extruder processing the blend to break the dispersed phase down into small droplets of small diameters as a result of the shear forces inside the extruder. These dispersed phase droplets are then elongated in the extruder due to the extensional flow field. The elongation of the droplets creates continuous fiber formation in the film with bonded points throughout the web. Branches tend to form from the fibers, and the branches cross over nearby fibers and bond to them. Washing the extruded film with the solvent removes the soluble polymer (such as PEO) and reveals these fibers and bonding points and creates a nonwoven fabric. Furthermore, the washing away of the soluble polymer phase leaves random, lengthy capillary channels for absorbing water. The air spaces left by the dissolved soluble polymer create bulk in the fabric.

The channels in the fabric are random in size and in shape lending themselves to heightened fluid intake and wicking. Water tends to be taken up by surface spreading through surface channels. Then the water is absorbed because channels tend to interconnect with one another through the depth of the fabric and along its length, so that water entering a channel on the surface of the fabric tends to be wicked by capillary action far into the fabric. The fabric retains the water it absorbs, subject to evaporation and physical forces applied to expel the water. Disposable personal care products produced from the resulting fabric would first be able to maintain structural integrity during extended storage and personal use while also being capable of being flushed in conventional sewage systems. Another advantage of the fabric is its silk-like surface texture, which makes the fabric ideal for positioning against the skin.

One procedure to make the non-soluble component (such as PE) the dispersed phase is to make it the minority constituent of the polymer blend. In such procedure, PEO as the continuous phase may be any molecular weight, but preferably has a low molecular weight, most preferably equal to or less than 200,000 g/mol. Thus, the nonwoven fabric of the present invention can be formed from a non-reactive blend of PE and PEO if the PE as the dispersed component is also the minority constituent. However, a fabric produced from a non-reactive blend is not wettable.

In another procedure, the nonwoven fabric can be formed from a non-reactive blend of the non-soluble and soluble components resulting in a unique phase morphology. In this alternative procedure, the PEO having a molecular weight of 100,000 g/mol or less and the PE and PEO are the majority and minority constituents respectively. With this latter procedure, a phase inversion will still occur with the PE remaining as the dispersed phase because of the lower molecular weight PEO.

According to a third procedure, a reactive blend of the soluble and non-soluble components may be processed in an extruder, resulting in a unique phase morphology in that the non-soluble phase is the volumetric majority while remaining as the dispersed phase in the blend and in the resulting film. To provide a reactive blend, the inventive process comprises the step of mixing the blend with a polar vinyl monomer and free radical initiator under conditions sufficient to graft a polar vinyl monomer onto both the soluble and insoluble polymer phases. When PEO is the soluble phase, grafting of the polar vinyl monomer improves the melt processability of the PEO such that the melt viscosity, melt pressure, and melt temperature are reduced. As a result, mixing in an extruder can maintain a majority constituent (such as PE) as the dispersed phase in the PEO. The level of grafting reaction influences the morphology of the nonwoven web formed by this process. Such grafting maintains a non-soluble, grafted polyolefin as the dispersed phase throughout the range of possible blend proportions of soluble to non-soluble components, regardless of whether the dispersed phase is the minority or majority constituent. The polyolefin is also grafted to about 0.1% to 5% by weight. Preferably, the polyolefin is grafted to about 0.2% to 5% by weight.

In a preferred embodiment, the polymer blend may comprise about 15 to 85 weight percent of a polyolefin and 85 to 15 weight percent of a polyethylene oxide. When the proportion of polyolefin is about 50–85 weight percent, a grafting monomer is added to the blend in an amount dictated by the total weight of polyolefin and polyethylene oxide, but preferably from about 1 weight percent to about 30 weight percent. More preferably, the content of the monomer in the blend comprises approximately 5 weight percent to approximately 20 weight percent. The polar vinyl monomers are unsaturated monomers containing at least one polar functional group such as an acid, ester, thiol, carboxyl, amino, carbonyl and hydroxyl groups. Acrylates and methacrylates groups are preferred polar groups and 2-Hydroxyethyl methacrylate and polyethylene glycol methacrylate are preferred polar vinyl monomer structures. The process for making reactive blends of polyolefins and polyethylene oxide is discussed in greater detail in U.S. Pat. No. 5,700,872 entitled "BLENDS OF POLYOLEFINS AND POLY(ETHYLENE OXIDE) AND PROCESS FOR MAKING THE BLENDS", the entire disclosure of which is incorporated herein by reference. From the reactive blends, cast films were extruded which were subsequently washed with water to remove the water-soluble portion of the blend which is grafted PEO. This results in a nonwoven fabric web composed of grafted polyolefin (such as grafted PE).

The thickness of the fabric can be varied to obtain different characteristics for different purposes. A thicker fabric is derived from a thicker film after washing the film with water. However, a thicker film takes longer to wash and is much stronger than thinner films. A thicker fabric will have a paper-like consistency and few, if any, pores extending completely through the fabric. Such a thicker fabric is wettable and highly absorbent. On the other hand, a thinner fabric wicks water more rapidly, and can pass water through pores to an absorbent layer adjacent to the fabric. Thus, thin versions of the fabric can be used as skin-friendly liners over an absorbent material in a garment. The thickness of the PE fibers in the fabric can be controlled by varying the proportion of PE in the polymer blend. Generally, a greater proportion of PE gives thicker PE fibers. Additional advantages will be apparent hereinafter.

The foregoing has outlined some of the pertinent objects and features of the invention. These should be construed to be merely illustrative of some of the more prominent features and applications of the intended invention. Many other beneficial results can be obtained by applying the disclosed invention in a different manner or by modifying the disclosed embodiments. Accordingly, other objects and a more comprehensive understanding of the invention may be obtained by referring to the detailed description of the preferred embodiment taken in conjunction with the accompanying drawings, in addition to the scope of the invention defined by the claims.

BRIEF DESCRIPTION OF THE DRAWINGS

For a more succinct understanding of the nature and objects of the present invention, reference should be directed to the following detailed description taken in connection with the accompanying drawings in which:

FIG. 1 illustrates one embodiment of the blending extruder, air-cooling unit and pelletizer in relationship to one another for practicing a portion of the present invention wherein grafting is necessary;

FIG. 2 illustrates one embodiment of the blending extruder, air-cooling unit, and pelletizer in relationship to one another for practicing a portion of the present invention wherein grafting in unnecessary;

FIG. 3 illustrates one embodiment of the extruder for converting the pellets into a precursor film from the steps of the system illustrated in either FIGS. 1 or 2;

FIG. 4 illustrates an alternative embodiment of the present invention wherein forming the blend and extruding the film may be carried out by the same extruder;

FIG. 5 illustrates one embodiment for implementing an automated washing and drying step;

DETAILED DESCRIPTION OF THE PREFERRED EMBODIMENTS

Figure 6:
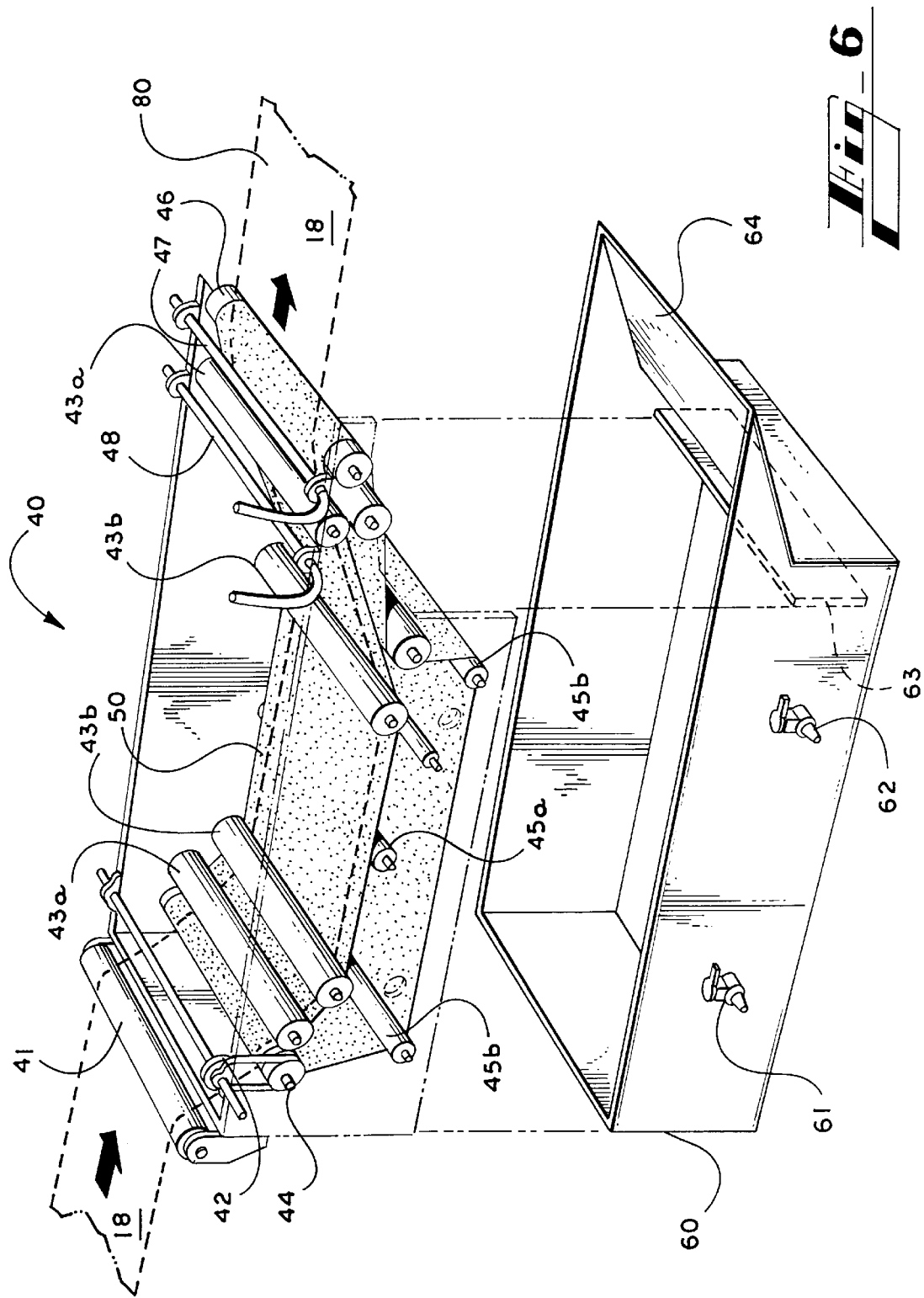
FIG. 6 illustrates in particular detail the washing device of FIGS. 4 and 5.

With reference to the drawings, the disclosed embodiments of the present invention relates to a nonwoven, porous fabric formed from extruded polyolefin and polyethylene oxide film. Polymer blends of polyolefins and polyethylene oxide have been shown to be water modifiable with or without grafting of one or more monomers. The film composition of the present invention made from these blends and having about 15 to 85 weight percent of a polyolefin and about 85 to 15 weight percent of a modified polyethylene oxide, is water-responsive. The resulting fabric, therefore, may be utilized in the manufacture of disposable personal hygiene articles. The inventors have produced a nonwoven fabric, formed from polymer composite materials, which lends itself to enhanced fluid intake and wicking. The novel fabric weakens in water such that personal hygiene articles may be flushed down conventional sewer systems after use.

In one embodiment of the present invention, the blend comprises about 15 weight percent to about 50 weight percent of a polyolefin and from about 50 weight percent to about 85 weight percent of polyethylene oxide. In this embodiment, wherein the polyolefin is the minority constituent in forming the blend, the film for producing the fabric may be obtained without grafting of a monomer.

In another embodiment, the nonwoven fabric can be formed from a non-reactive blend of the non-soluble and soluble components resulting in a unique phase morphology where the PE and PEO are the majority and minority constituents respectively. In this embodiment, the PEO must have a molecular weight of 100,000 g/mol or less. Thus, with this latter procedure, a phase inversion will still occur with the PE remaining as the dispersed phase because of the lower molecular weight PEO.

In a third embodiment of the present invention, the blend comprises about 50 weight percent to about 85 weight percent of a modified polyolefin and from about 50 weight percent to about 15 weight percent of modified polyethylene oxide. The amount of polar vinyl monomer added to the blend is dictated by the total weight of polyolefin and polyethylene oxide but is preferably from about 1 weight percent to about 20 weight percent. As a result of grafting the monomer, processing the reactive blend results in the unique inverse phase morphology wherein the polyolefin phase is the dispersed phase. Moreover, the grafting of the monomer imparts permanent wettability to the resulting fabric. However, fabric produced from other than reactive blends still have enhanced fluid intake and wicking without grafting.

Wettability is an effect of chemical composition rather than physical structure. Whether a surface is "wettable" or not depends on how much water beads up on the surface. A material is non-wettable if beads of water form upon a surface and the resulting contact angle between the surface and the water is greater than 90 degrees. On the other hand, a surface is wettable where beads of water are spread over the surface and the contact angle is less than 90 degrees. Preferably, the contact angle is closer to zero to be more wettable. Surfaces which are merely wettable as compared to being permanently wettable are surfaces where eventually the wettablity may be washed away. A permanently wettable fabric does not have changing surface wettability characteristics. On the other hand, a non-permanent wettable surface, such as a non-wettable surface coated or treated with a surfactant, losses surface wettability upon washing with water. It is important to note that enhanced fluid intake and wicking may be characteristics of a fabric according to the present invention, even when the fabric is not wettable because no grafting monomer has been added to the components.

Preferably, the content of polyethlene in the blend comprises approximately 30% to 80% by weight. More preferably, the content of polyethylene in the blend comprises approximately 50% to 75% by weight.

The saturated ethylene polymers useful in the practice of this invention are homopolymers or copolymers of ethylene and are essentially linear in structure. As used herein, the term "saturated" refers to polymers which are fully saturated, but includes polymers containing up to about 5% unsaturation. The homopolymers of ethylene include those prepared under either low pressure, i.e., linear low density polyethylene, or high pressure, i.e., branched or low density polyethylene. The high density polyethylenes are generally characterized by a density that is about equal to or greater than 0.94 grams per cubic centimeter (g/cc). Generally, the high density polyethylenes useful as the base resin in the present invention have a density ranging from about 0.94 g/cc to about 0.97 g/cc. The polyethylenes can have a melt index, as measured at 2.16 kg and 190° C., ranging from about 0.005 decigrams per minute (dg/min) to 100 dg/min. Desirably, the polyethylene has a melt index of 0.1 to 20 dg/min. Alternatively, mixtures of polyethylene can be used as the base resin in producing the graft copolymer compositions, and such mixtures can have a melt index greater than 0.005 dg/min to less than about 100 dg/min.

The low density polyethylene has a density of less than 0.94 g/cc and is usually in the range of 0.91 g/cc to about 0.93 g/cc. The low density polyethylene has a melt index ranging from about 0.05 dg/min to about 100 dg/min and desirably from 0.05 dg/min to about 20 dg/min. Ultra low density polyethylene can be used in accordance with the present invention. Generally, ultra low density polyethylene has a density of less than 0.90 g/cc.

The above polyolefins can also be manufactured by using the well known multiple-site Ziegler-Natta catalysts or the most recent single-site metallocene catalysts. The metallocene catalyzed polyolefins have better controlled polymer microstructures than polyolefins manufactured using Ziegler-Natta catalysts, including narrower molecular weight distribution, well controlled chemical composition distribution, co-monomer sequence length distribution, and stereoregularity. Metallocene catalysts are known to polymerize propylene into atactic, isotactic, syndiotactic, isotactic-atactic stereoblock copolymer.

Copolymers of ethylene which can be useful in the present invention may include copolymers of ethylene with one or more additional polymerizable, unsaturated monomers. Examples of such copolymers include, but are not limited to, copolymers of ethylene and alpha olefins (such as propylene, butene, hexene or octene) including linear low density polyethylene, copolymers of ethylene and vinyl esters of linear or branched carboxylic acids having 1–24 carbon atoms such as ethylene-vinyl acetate copolymers, and copolymers of ethylene and acrylic or methacrylic esters of linear, branched or cyclic alkanols having 1–28 carbon atoms. Examples of these latter copolymers include ethylene-alkyl (meth) acrylate copolymers, such as ethylene-methyl acrylate copolymers.

Polyethylene oxide polymers suitable for the present invention can have a molecular weight ranging from 100,000 to 8,000,000 and preferably, a range from about 100,000 to about 400,000. Polyethylene oxide is available from Union Carbide Corporation under the trade name of POLYOX®. Typically, polyethylene oxide is a dry free flowing white powder having a crystalline melting point in the order of about 65° C., above which polyethylene oxide resin becomes thermoplastic and can be formed by molding, extrusion and other methods known in the art.

To prepare the grafted polyethylene and grafted polyethylene oxide constituents of the film of the invention, the polyolefin and polyethylene oxide are reacted with the polar vinyl monomer in the presence of a free radical initiator. The initiator serves to initiate free radical grafting of the monomer. The method of grafting the polymer blends includes melt blending the desired weight ratios of a mixture of the polyolefin, polyethylene oxide, the monomer and a free radical initiator in an extruder and at a reaction temperature where the polyolefin and polyethylene oxide are converted to a polymer melt. Accordingly, a preferred method includes adding the polyolefin, polyethylene oxide, monomer and free radical initiator simultaneously to the extruder before the polymer constituents, i.e., the polyolefin and polyethylene oxide, have been melted. Desirably, the melt extruder used for melt blending can introduce various constituents into the blend at different locations along the screw length. For example, the free radical initiator, cross-linking agents, or other reactive additives can be injected into the blend before or after one or more of the polymer constituents is melted or thoroughly mixed. More preferably, the polyolefin and polyethylene oxide are added at the beginning of the extruder. After melting, the monomer is added to the melted polymers and farther down the extruder barrel, the free radical initiator is fed to the melt blend.

The polyolefin (such as polyethylene) and polyethylene oxide comprising the film having grafted thereto an effective amount of monomer which unexpectedly produces in the film an inverse phase morphology. The polyolefin may be the major constituent. One skilled in the art would expect the polyethylene, as the major constituent, to form the continuous phase where the polyethlene oxide is distributed therein as the discontinuous phase. However, the present film has the grafted polyethlene oxide as the continuous phase with the grafted polyethylene distributed as the discontinuous phase notwithstanding that there is a greater amount of polyethylene. The inverse phase morphology of the present film is described in greater detail in copending U.S. patent application having U.S. Ser. No. 08/855,324 filed on May 13, 1997 and entitled "BLENDS OF POLYETHYLENE AND PEO HAVING INVERSE PHASE MORPHOLOGY AND METHOD OF MAKING THE BLENDS", the entire disclosure of which is incorporated herein by reference.

The free radical initiators which can be used to graft the monomer onto the polyolefin include acyl peroxides such as benzoyl peroxide; dialkyl; diaryl; or aralkyl peroxides such as di-t-butyl perioxide; dicumyl peroxide; cumyl butyl peroxide; 1,1-di-t-butyl peroxy-3,5,5-trimethylcyclohexane; 2,5-dimethyl-2,5-di(tbutylperoxy) hexane; 2,5-dimethyl-2, 5-bis(t-butylperoxy) hexyne-3 and bi(s-t-butyl peroxyisopropylbenzene); peroxyesters such as t-butyl peroxypivalate; t-butyl peroctoate; t-butyl perbenzoate; 2,5-dimethylhexyl-2,5-di(perbenzoate); t-butyl di(perphthalate); dialkyl peroxymonocarbonates and peroxydicarbonates; hydroperoxides such as t-butyl hydroperoxide, p-methane hydroperoxide, pinane hydryoperoxide and cumene hydroperoxide and ketone peroxides such as cyclohexanone peroxide and methyl ethyl ketone peroxide. Azo compounds such as azobisisobutyronitrile may also be used.

The amount of free radical initiator added to the extruder should be an amount sufficient to graft from about 1 percent to 100 percent of the monomer onto the polyolefin and polyethylene oxide. This ranges from about 0.1 weight percent to about 10 weight percent of initiator, and preferably, from about 0.1 weight percent to about 5 weight percent wherein all such ranges are based on the amount of monomer added to the melt blend. The method of grafting polar groups onto polyethylene and polyethylene oxide is also described in greater detail U.S. Pat. No. 5,700,872 entitled "BLENDS OF POLYOLEFIN AND POLYETHYLENE OXIDE AND PROCESS FOR MAKING THE BLENDS". Moreover, the grafting of polar groups onto polyethylene and polyethylene oxide is described in greater detail in copending U.S. patent applications having U.S. Ser. No. 08/733,410 filed on Oct. 18, 1996 and entitled "METHOD OF MAKING POLYOLEFIN HAVING GREATER THAN 5% 2-HYDROXYETHYL METHACRYLATE AND GRAFTED THERETO", and U.S. Ser. No. 08/733,551 filed on Oct. 18, 1996 and entitled "POLYOLEFIN HAVING GREATER THAN 5% 2-HYDROXYETHYL METHACRYLATE AND GRAFTED THERETO", the entire disclosures of which are incorporated herein by reference.

The present invention is illustrated in greater detail by the specific examples presented below. It is to be understood that these examples are illustrative embodiments and are not intended to limit the invention, but rather are to be construed broadly within the scope and content of the appended claims.

Blending of a Comparative Example

FIGS. 1 and 2 each illustrate one embodiment of the blending portion of the system 10 (FIG. 4) carried out during the inventive process. For a Comparative Example, a 60/40 weight percent resin blend of low density polyethylene (PE) and polyethylene oxide (PEO) was melt blended using an extruder 11a as shown in FIG. 2. The PE had a melt index of 1.9 decigrams per minute (dg/min) and a density of 0.917 grams per cubic centimeter (g/cc) (Dow 503I; available from Dow Chemical Company, Midland, Mich.). The PEO had a reported molecular weight of 200,000 g/mol (POLYOX® WSRN-80; available from Union Carbide Corporation). The extruder 11a used for making the blend was a Werner & Pfleiderer ZSK-30 extruder (available from Werner & Pfleiderer Corporation, Ramsey, N.J.). The extruder 11a may have multiple processing barrels allowing additional materials to be added while making the blend. The extruder 11a used during the present process had 14 processing barrels available as illustrated in FIGS. 1 and 2.

The resin blend was fed to the extruder 11a at a rate of 34 lb./hr. The extruder had a pair of co-rotating screws arranged in parallel. The center distance between the two shafts was 26.2 mm. The nominal screw diameter was 30 mm. The actual outer screw diameter was 30 mm. The inner screw diameter was 21.3 mm. The thread depth was 4.7 mm. The extruder 11a had 14 processing barrels, with 13 heated barrels divided into 7 heating zones. The overall processing length was 1338 mm. The seven heating zones were all set at 180 degrees Centigrade (°C.). The screw speed was set at 300 rpm. FIG. 2 illustrates the initial blending of the Comparative Example in the extruder 11a which is subsequently pelletized into pellets 32 to be received in extruder 11b as shown in FIG. 3 and discussed below. However, the film from the blend having PEO of a molecular weight of 200,000 g/mol without reactive blending, produced as described below, could not be washed with water to produce a nonwoven fabric. The resulting film was not wettable by water and behaved like a typical PE film.

Blending of Examples 1–11 (reactive, wettable)

For examples 1–11, a 60/40 weight percent resin blend of PE and PEO, as described in the Comparative Example, was fed to the ZSK-30 multi-chambered extruder 11a as shown in FIG. 1. Examples 1–11 are reactive blends of PE and PEO with PEG-MA and free radical initiator. The PEO has a molecular weight of 200,000 g/mol. The temperature settings and screw speed for the Examples are specified in Table 1. The resin rates are specified in Table 2.

At barrel 4 of the extruder 11a, a monomer, polyethylene glycol methacrylate (PEG-MA; catalog no. 40,954–5 with a molecular weight of 246 grams/mole; available from Aldrich Chemical Company, Milwaukee, Wis.) was added at the rated specified in Table 2. At barrel 5 of the extruder 11a, a free radical initiator (2,5-dimethyl-2,5-di(tbutylperoxy) hexane, supplied by Atochem, 2000 Market St., Philadelphia, Pa. under the trade name LUPERSOL® 101 or otherwise known as L101) was added at the rate specified in Table 2.

The films from examples 1–11 had phase inversion and could be washed with water to produce a nonwoven fabric as described below. Examples 1–11 from extruder 11a are subsequently pelletized in the pelletizer 30 to form pellets 32. The pellets 32 are then to be received in extruder 11b for extruding films as shown in FIG. 3 and discussed below.

TABLE 1

| Example | Set Temp. for all Zones (° C.) | Screw Speed (rpm) |
| --- | --- | --- |
| 1 | 180 | 300 |
| 2 | 180 | 300 |
| 3 | 180 | 300 |
| 4 | 190 | 300 |

TABLE 1-continued

| Example | Set Temp. for all Zones (° C.) | Screw Speed (rpm) |
| --- | --- | --- |
| 5 | 200 | 300 |
| 6 | 180 | 300 |
| 7 | 180 | 300 |
| 8 | 180 | 200 |
| 9 | 180 | 300 |
| 10 | 180 | 400 |
| 11 | 180 | 500 |

TABLE 2

| Example | Resin Rate (lb/hr) | Monomer Rate (lb/hr) | Initiator Rate (lb/hr) |
| --- | --- | --- | --- |
| 1 | 34 | 3 | 0.2 |
| 2 | 34 | 5.5 | 0.3 |
| 3 | 34 | 9 | 0.5 |
| 4 | 35 | 3 | 0.2 |
| 5 | 35 | 3 | 0.2 |
| 6 | 25 | 3 | 0.2 |
| 7 | 30 | 3 | 0.2 |
| 8 | 35 | 3 | 0.2 |
| 9 | 35 | 3 | 0.2 |
| 10 | 35 | 3 | 0.2 |
| 11 | 35 | 3 | 0.2 |

Blending of Example 12 (non-reactive, non-wettable)

A 60/40 weight percent resin blend of PE and polyethylene oxide having a reported molecular weight of 100,000 g/mol (POLYOX® WSRN-10), without reactive blending, was fed to a ZSK-30 extruder 11a, as shown in FIG. 2, at a rate of 35 lb./hr. No monomer or initiator was added. The seven heating zones were all set at 180° C. The screw speeed was set a 300 rpm. Example 12 is also pelletized in pelletizer 30 to form pellets 32 as shown in FIG. 4. The film from Example 12, with a lower molecule weight of 100,000 g/mol, produced as described below, did have phase inversion when extruded from extruder 11b and could be washed with water to produce a nonwoven fabric as described below.

Blending of Example 13 (reactive, wettable)

A 30/70 weight percent resin blend of low density polyethylene (PE, Dow 5031) and polyethlene oxide (PEO, POLYOX® WSRN-80) was melt blended using the extruder 11a. The extruder used for making this end was also a HAAKE counter-rotating twin screw extruder equipped with a two-hole strand die. The extruder had a length of 300 millimeters. Each conical screw had a 30 millimeter diameter at the feed port and a diameter of 20 millimeters at the die. The extruder 11a had four heating zones set at 170, 180, 180 and 190 degrees Centigrade. The screw speed was 150 rpm. The resin blend was feed to the extruder at a rate of 5 lb/hr. Contemporaneously with the polymer feed, PEG-MA was added at a rate of 0.5 lb/hr and L101 was added at 0.025 lb/hr. The polymer was extruded, cooled in air and pelletized. The film from Example 13, produced as described below, did not have phase inversion when extruded from extruder 11b because the PE was the minority constituent. But the film could be washed with water to produce a nonwoven fabric. When washed, the resulting nonwoven fabric had the appearance and characteristics similar to the 60/40 PE/PEO blends and reactive blends of the preceding examples. However, the resulting fabric did possess some notable differences in that the fabric was finer with fewer fibers while producing a weaker less bonded web. Also, the fabric is very soft. These differences are primarily attributed to a lesser amount of PE.

Blending of Example 14 (reactive, wettable)

An 80/20 weight percent resin blend of PE and PEO was melt blended using the Haake extruder 11a. As before, the extruder 11a had four heating zones set at 170, 180, 180, and 190 degrees Centigrade. The screw speed was 150 rpm. The resin blend was fed to the extruder at a rate of 5 lb/hr. Contemporaneously with the polymer feed, PEGMA was added at a rate of 0.5 lb/hr and L101 was added at 0.025 lb/hr. The polymer was extruded, cooled in air and pelletized. The film from this example also had phase inversion when extruded from extruder 11b and could be washed with water to produce a nonwoven fabric. When washed, the resulting nonwoven fabric produced from Example 14 also had the appearance and characteristics similar to the 60/40 PE/PEO reactive blends and the reactive blends of the preceding examples. Also, the fabric was a lot tighter.

Film Propessing

The films of the reactive blends of this invention may be prepared by both a cast film extrusion process or a blown film extrusion process but is not limited thereto. All films of the melt blends in the Comparative Example and Examples 1–14 were made using a Haake counter-rotating twin screw, multi-chambered extruder 11b (available from Haake, 53 West Century Road, Paramus, N.J. 07652) equipped with a four or eight inch slit die. The extruder 11b had a length of 300 mm. The conical screws had 30 mm diameter at the feed port and a diameter of 20 mm at the film die 14. The extruder 11b had four heating zones set at 170, 180, 180, and 190° C.

As shown in FIG. 3, the second extruder 11b receives the pellets 32. Within the extruder 11b, the pellets are melted and mixed. The blend will have a phase morphology in which the PE is the dispersed phase while being extruded into the films of Examples 1–14 through film die 14. The pellets 32 formed from the Comparative Example will not have an inverse phase morphology but could be extruded into a film nonetheless. Alternatively, the initial blending of the polymer blend and the subsequent extrusion into the desired film, both functions previously described as being separately performed in extruders 11a and 11b respectively, may be simultaneously conducted in an extruder 11. FIG. 4 illustrates the extruder 11 wherein the blends of Examples 1–14 are formed with PE as the dispersed phase and are extruded into film 18.

When two extruders are used and the extruder 11a produces pellets, in an optional embodiment of the method of producing the present invention, the extruded strands from the extruder 11a are air-cooled as they exit the extruder 11a as shown in either FIG. 1 or 2. The strands drop down to an air-cooling unit 20 which blows air directly onto the strands. The air-cooling unit 20 uses multiple fans 21 to blow the air which may be chilled or at ambient temperature. The belt 22 of the air-cooling unit 20 moves in the direction of flow of the strands towards a pelletizer 30. The pelletizer 30 pelletizes the strands into pellets 32.

In one embodiment as shown in either of FIGS. 3 or 4, the extruded film 18 from the extruder 11b (or from a single extruder) is drawn to reduce its thickness onto a chill-roll 16 where it is cooled and collected as a film 18 of 4–5 mils. Preferably, the chill roll 16 is operated at a speed sufficient to wind up a film having a thickness of about 4 mils (about 0.004 inch) and is maintained at a temperature of 15–20° C.

Although the use of particular extruders is disclosed in the preferred embodiment, other methods of processing are encompassed by the present invention. The preferred form has been made only by way of example and it should be realized by those skilled in the art that equivalent processing steps may be utilized without departing from the spirit and scope of the invention.

Film Washing

According to the method of the invention, a nonwoven fabric 80 may be produced, as shown in FIGS. 4–6. This novel process is superior to other existing processes for making polyethylene fabric in that the present invention does not need a spinneret nor does it need any non-aqueous solvents which could cause environmental concerns. This process also forgoes the fiber drawing operation typically associated with these other known processes.

In order to treat the film 18 and remove the soluble PEO phase to produce the nonwoven fabric 80, the film 18 is soaked in water. One method to remove the PEO involves submerging the film 18 in water for about 6 minutes so that the continuous phase of water-soluble PEO is substantially removed. The remaining PE-based nonwoven fabric is rinsed with water and laid flat to dry on a paper towel or other absorbent material. Alternatively, the fabric can be dried by a vacuum dewatering device or by a heated drum process.

Alternatively, the film may be run through a semiautomated water bath with nip rolls and a wire carrier. The film is submerged in water for about 2 minutes, turned over and submerged for another 2 minutes. The bath is equipped with a rinse at the end and the fabric is again dried on a air cooling belt with a wire carrier or by any of the above-identified drying methods.

FIG. 6 illustrates one version of a washing device 40 which may be used to practice the present invention. The film 18 is received into the washing device 40 over a roller 41 and deposited onto a continuous belt 50. The belt 50 is driven by a drive pulley 42 which may be operated by hand or by a motor (not shown). The drive 42 drives a roller 44 which contacts the belt 50. Four idler rollers 43a, 43b hold the film 18 down on and in contact with the belt 50 as the film 18 is fed through the washing device 40.

The belt 50 is positioned within a tank 60. Water (not shown) is fed into the tank 60 though an inlet 61 and out through an outlet 62. Water flow through the tank 60 is continuous during operation. The water should be maintained within a temperature in which the soluble polymer is soluble, and thus may be maintained at ambient temperatures in the case of PEO which is soluble at ambient temperatures. The water level in the tank 60 should be maintained just above the two lower rollers 43b. The two lower rollers 43b keep the film 18 in contact with the belt 50 and under the water to allow the water soluble resins to be dissolved. A plurality of idler rollers 45 maintain the belt at its proper tension. An upper, center roller 45a acts as a top tension adjustment. A pair of lower rollers 45b act as outer tension adjustments. Together, the rollers 45 adjust tracking and control belt sag.

A rinser 48 rinses the resulting fabric with a curtain of water as it emerges from the bath of water. A high pressure water curtain is used to clean any dissolved water soluble resin from the film web. The water and the dissolved water-soluble resin are carried into the tank 60 by the sloped end wall 64 of the tank 60. A baffle 63 in the tank restricts the movement of rinse water and dissolved material and directs it toward the outlet 62. The water should be continuously cleaned of the dissolved solids by a separation system (not shown) downstream of the outlet 62. New cleaned water may be introduced through the rinser 48 to maintain the water level in the tank 60. An air knife 47 removes excess water from the fabric just before it leaves the washing device 40 over a roller 46. All rinse water removed by the air curtain is returned to the tank 60 by the sloped end wall 64.

The inventors envision any number of different ways to wash the film with water to remove the PEO. One such way would be to wash the film with an automated water bath that does not need a wire carrier so that the film could be uniformly exposed to water.

As shown in FIG. 5, once the resulting fabric exits the washing device 40, the fabric can be wound on a rewind reel 70 to produce a roll of any diameter.

FIGS. 7–10 illustrate the fiber web of the present invention. Characteristic of the thermoplastic PE/PEO reactive blend film of the present invention, views using a scanning electron microscope and using back-scattered electron detector images show that the polyethylene oxide forms the continuous phase wherein the modified polyolefin is in a discontinuous phase, that is, dispersed throughout the grafted polyethylene oxide phase. A constituent having a lower atomic number produces a lower intensity of back-scattered electron microscope imaging as described in greater detail in Linda C. Sawyer and David T. Grubb, Polymer Microscopy, Chapman & Hall, London, 1987, p. 25. Desirably, the polyolefin portions of the thermoplastic film have an average cross-sectional diameter ranging from about 0.1 microns to about 50 microns, preferably from about 0.5 microns to about 30 microns and more preferably from about 0.5 microns to about 25 microns. Such "polyolefin portions" can be solidified pockets of polyolefin, fibers or combinations thereof.

Briefly, the film produced as a result of the present invention is water modifiable. As used herein, water modifiable means that when a film is immersed in water under the described conditions, the water removes the soluble phase. Water modifiable polyolefin-containing films are described in greater detail in copending U.S. patent application having U.S. Ser. No. 08/813,571 filed on Mar. 6, 1997 and entitled "WATER-MODIFIABLE FLUSHABLE POLYOLEFIN-CONTAINING FILM", the entire disclosure of which is incorporated herein by reference.

Figure 7:
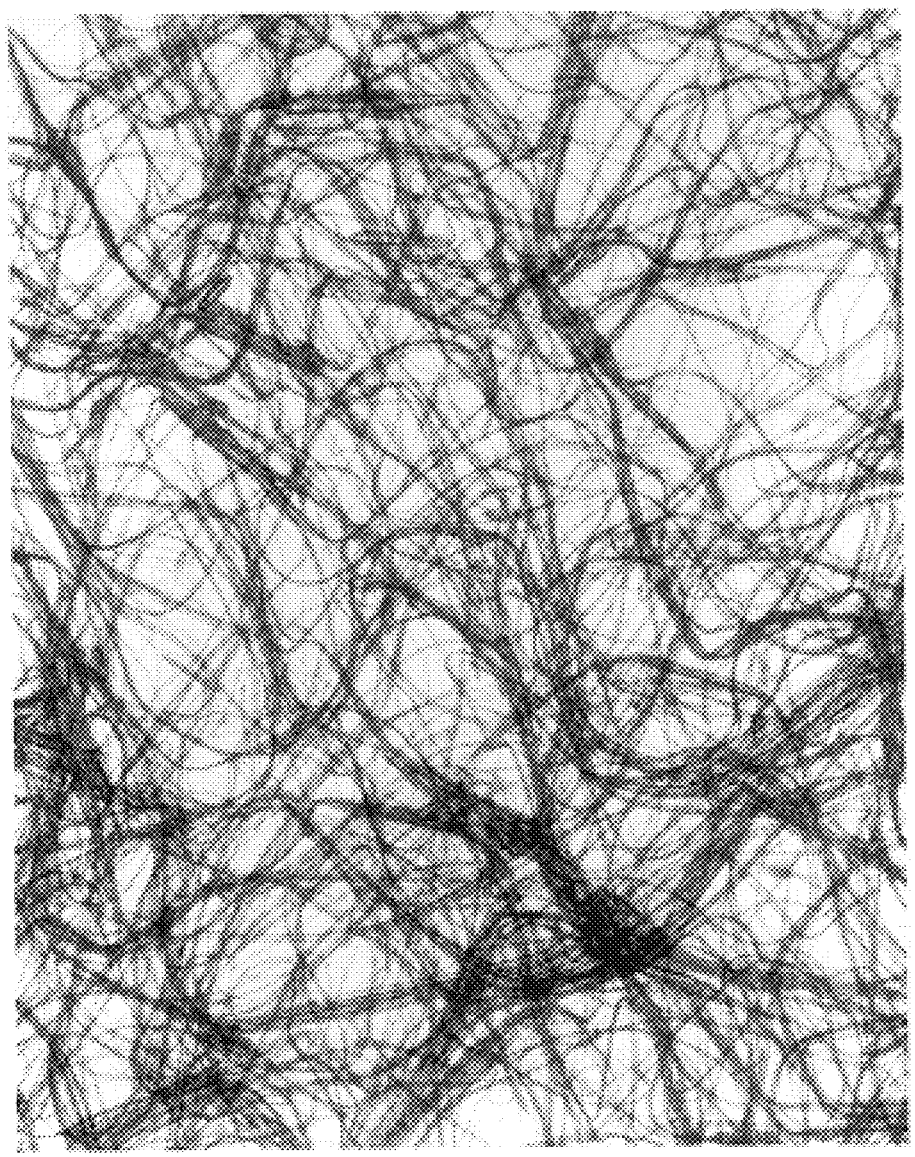
FIG. 7 is an optical micrograph at 30X of the typical fiber web pulled apart by hand to expose individual fibers made from a reactive blend.
Figure 8:
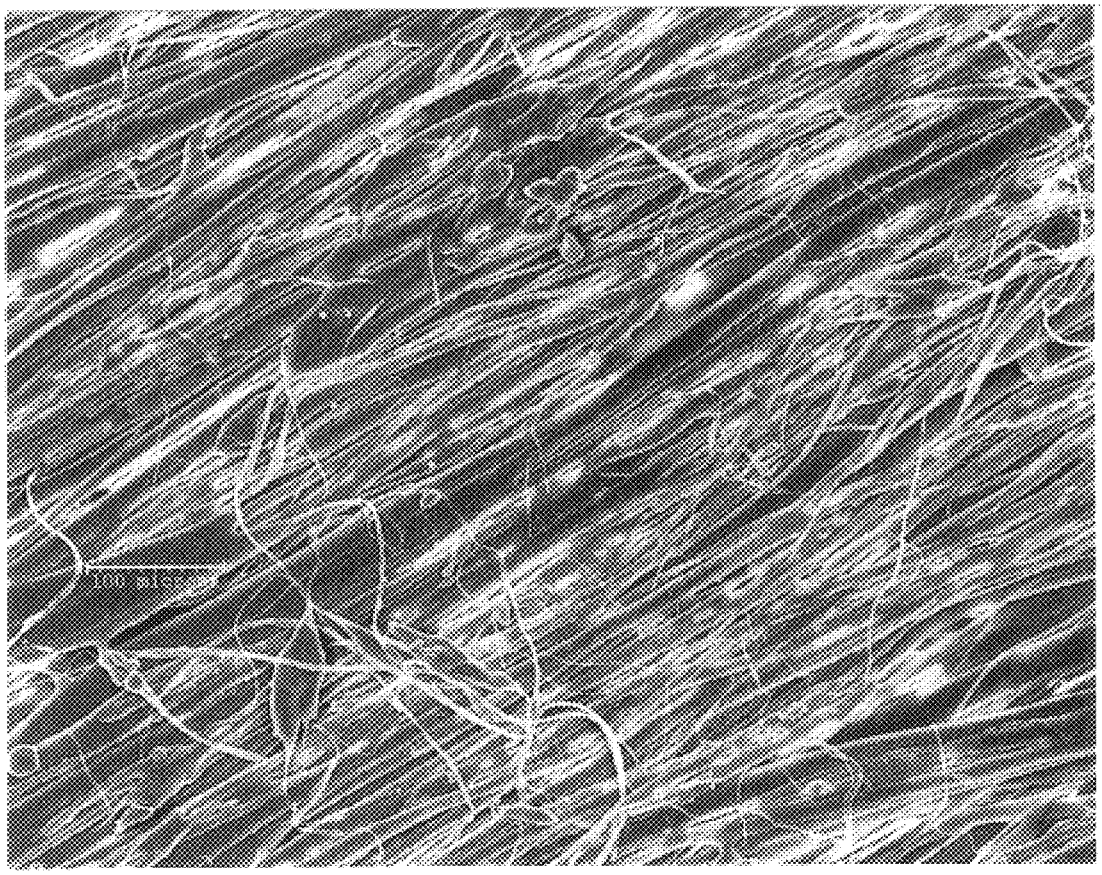
FIG. 8 is a scanning electron micrograph at 150X of the typical unopened fiber web made into a film and treated with a solvent.
Figure 9:
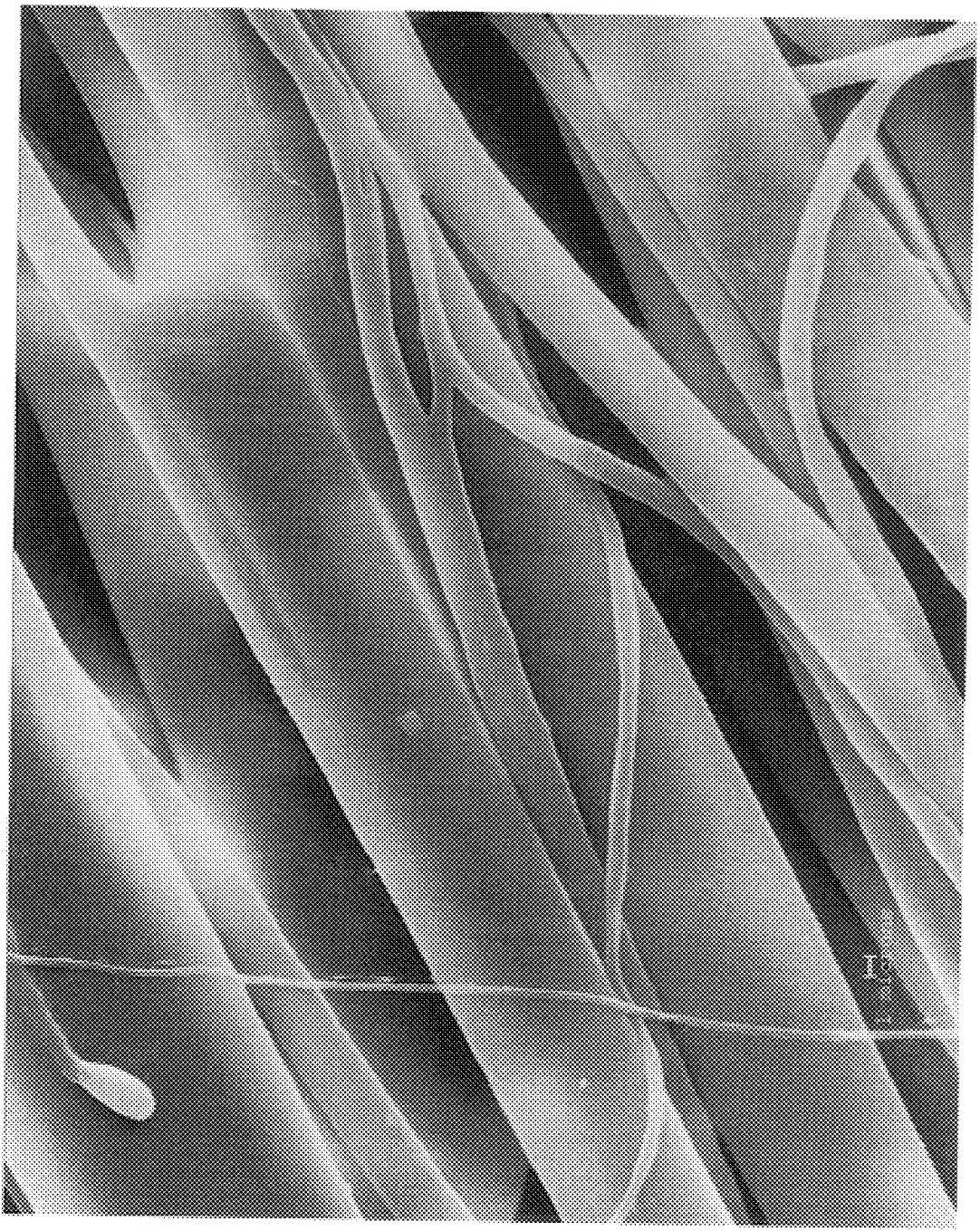
FIG. 9 is a scanning electron micrograph at 2000X illustrating in particular varying fiber size and shape and fiber branching in an unopened fabric of the present invention.
Figure 10:
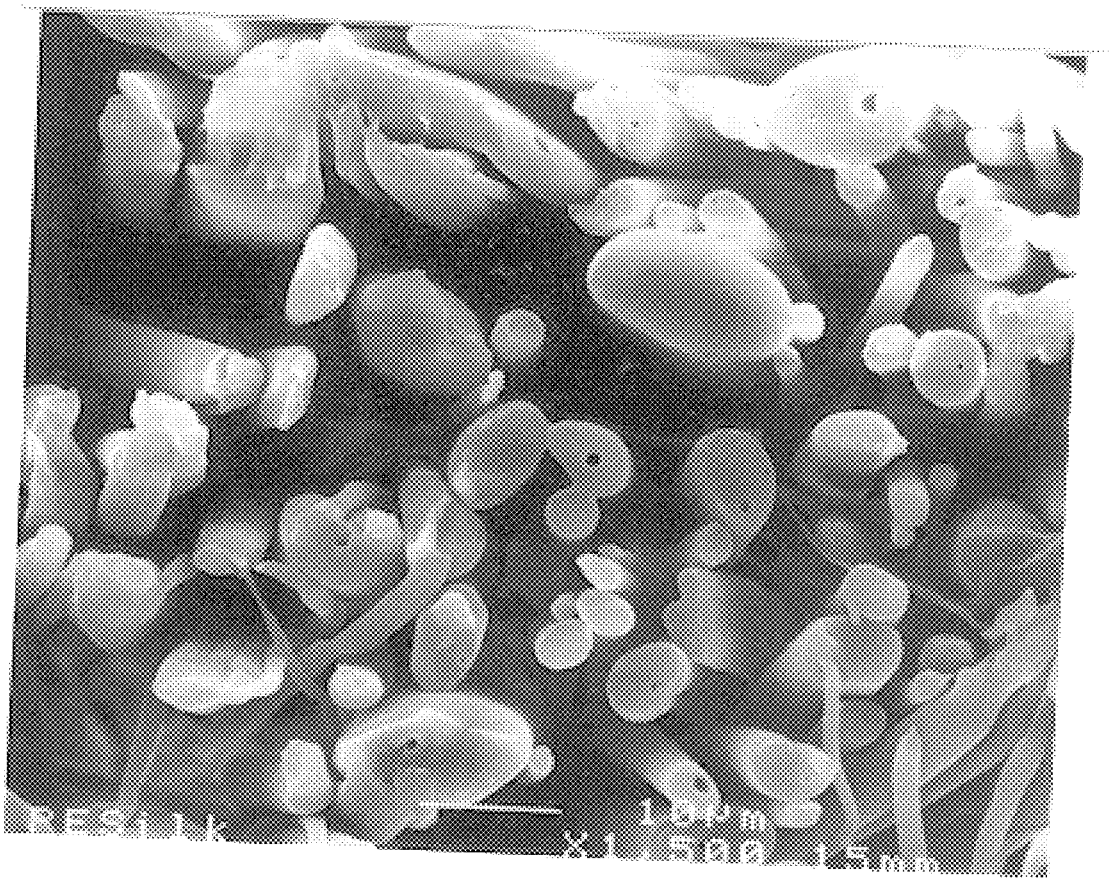
FIG. 10 is a scanning electron micrograph at 1500X illustrating a typical cross-section of the fabric of the present invention after being pulled apart by hand to expose individual fibers.

The fiber web illustrated in FIG. 7 has been pulled apart by hand to better illustrate the structure of the web, and in particular, to illustrate the continuous fiber formation with multiple bonded points throughout the web. FIGS. 8 and 9 best illustrate the lengthy, randomly sized and shaped capillary channels for absorbing and transporting water. FIG. 10 is a cross-sectional view of the fabric web produced by the present invention which illustrates the microstructure of each of the fibers of the continuous web. As can be seen in FIG. 10, the individual fibers may have holes or microcapillaries extending within the fibers.

The PE fibers in the web tend to be directionally oriented along a longitudinal axis, as shown in FIGS. 8 and 9. The fibers vary widely in diameter and shape. Some are circular in cross section, some oval, some irregular, and some ribbon-like. As the film is extruded prior to washing to form the fabric web, the fibers tend to branch, and the branches can be seen lying across multiple, neighboring fibers in the figures. Thermal bonds are created during extrusion and drawing at intermittent points between adjacent and crossing fibers and between branches and the fibers they lie across.

The spaces or channels formed between the fibers also vary widely in cross sectional shape. The channels are elongated and extend generally parallel to the longitudinal axis on the surface and within the fabric. A substantial portion of the channels are interconnected to one another. In the case of reactive blends, where the polyolefin and the polyethylene oxide is grafted as described hereinabove, the resulting fabric is permanently wettable.

A nonwoven, porous fabric according to the present invention has the following characteristics:

elongated fibers of polyolefin substantially oriented along a longitudinal axis;

a plurality of branches of the fibers extending across multiple fibers in the fabric;

thermal bonds formed between adjacent fibers and between the branches and fibers crossed by the branches;

elongated channels extending generally parallel to the longitudinal axis on the surface of the fabric and within the fabric, a substantial proportion of the channels being interconnected to other channels;

enhanced fluid intake and wicking;

a silk-like hand and shine; and permanent wetness with regard to reactive blends (grafting).

These characteristics can be seen in the optical and scanning electron micrographs of FIGS. 7–10. Furthermore, large pieces of the fabric (for example, diaper-sized or larger), can be flushed through waste water disposal systems without blocking or clogging such systems, because the fabric is wettable, soft, flexible, and slick.

The characteristics of the resulting fabric are presented in Tables 3–5 below. In summary, the ideal fabric includes internal voids averaging in a range from about 3% to about 51% of the volume of the fabric. The preferred fabric should have surface pores having an average open area in a range from about 5% to about 24%. Also, the preferred fabric should have surface pores having an average equivalent hydraulic diameter in a range from about 1.5 micrometers to about 40 micrometers and an average equivalent circular diameter in a range from about 1.5 micrometers to about 40 micrometers. There is a great variety of surface structure and fiber distribution in the fabric of the present invention.

TABLE 3

Summary Table of Surface Porosity Data
(Examples 1–11)

| Sample I.D. | % Area (%) | Aniso-tropy (−) | Equivalent Hydraulic Diameter (μm) | A-wtd EHD (μm) | Equivalent Circular Diameter (μm) | Vol-wtd EHD (μm) |
|---|---|---|---|---|---|---|
| 1 | 22.7 | 0.56 | 4.4 | 9.3 | 7.8 | 12.5 |
| 2 | 13.2 | 0.43 | 3.7 | 6.4 | 6.2 | 7.8 |
| 3 | 23.6 | 0.44 | 4.3 | 8.4 | 7.8 | 10.8 |
| 4 | 18.2 | 0.55 | 4.2 | 8.8 | 7.5 | 11.3 |
| 5 | 5.8 | 0.71 | 3.8 | 7.6 | 6.1 | 10.5 |
| 6 | 14.5 | 0.57 | 4.0 | 7.7 | 7.0 | 9.5 |
| 7 | 22.5 | 0.57 | 3.8 | 8.0 | 6.7 | 10.6 |
| 8 | 17.3 | 0.52 | 3.7 | 6.2 | 6.2 | 7.6 |
| 9 | 17.0 | 0.49 | 3.9 | 6.7 | 6.8 | 8.0 |
| 10 | 10.5 | 0.47 | 3.6 | 5.4 | 5.9 | 6.2 |
| 11 | 24.0 | 0.51 | 4.4 | 8.0 | 8.1 | 9.3 |

TABLE 4

Summary Table of Average Fiber Diameter Statistics
from Surface Images
(Examples 1–11)

| Sample I.D. | Ave "Fiber Diam" (μm) | Standard Deviation on 12 fields (μm) | Standard Error |
|---|---|---|---|
| 1 | 13.1 | 1.5 | 0.5 |
| 2 | 17.8 | 3.4 | 1.0 |
| 3 | 11.5 | 1.7 | 0.5 |
| 4 | 16.6 | 3.8 | 1.1 |
| 5 | 47.7 | 16.8 | 4.9 |
| 6 | 21.1 | 8.1 | 2.4 |
| 7 | 13.3 | 3.0 | 0.9 |
| 8 | 13.2 | 2.0 | 0.6 |
| 9 | 14.8 | 2.0 | 0.6 |
| 10 | 20.9 | 6.9 | 2.0 |
| 11 | 11.5 | 1.7 | 0.5 |

The Fiber Diameter listed in Table 4 is based on the method of metallurgical grain size, obtained by dividing the field area by the field horizontal projection length, or in this case, the field area by the field vertical intercept count. Since individual fibers could not be easily and automatically isolated, this method was needed.

TABLE 5

Summary Table of Cross-sectional Analysis
(Examples 1–11)

| Sample I.D. | Ave % Voids | Debond Void Thickness, μm | Total Section Thickness, μm | Ave # Protruding Fibers/mm | Onset Thickness, μm |
|---|---|---|---|---|---|
| 1 | 51 | 48 | 95 | 10.5 | 168 |
| 2 | 38 | 40 | 106 | 7.6 | 166 |
| 3 | 44 | 74 | 168 | 9.5 | 269 |
| 4 | 50 | 44 | 87 | 11.1 | 152 |
| 5 | 3 | 2 | 67 | 4.3 | 105 |
| 6 | 31 | 24 | 76 | 6.9 | 134 |
| 7 | 46 | 49 | 104 | 7.5 | 2&3 |
| 8 | 44 | 25 | 56 | 7.2 | 115 |
| 9 | 48 | 43 | 89 | 6.1 | 156 |
| 10 | 38 | 22 | 58 | 6.5 | 111 |
| 11 | 47 | 31 | 65 | 12.9 | 121 |

The surface characteristic of Samples 1–11 as presented in Tables 3–5 may be summarized as follows. The samples were examined with the Backscattering Electron/High Contrast (BSE/HICON) method with photomontages of planar surfaces in both XY and YZ directions. The conditions chosen for making the samples created large differences in surface porosity, fiber diameters Z-directional thickness, and internal void content. In short, Sample 11 had the highest surface porosity but not the largest mean pore size. Sample 1 had the largest mean surface pore size. Sample 11 also had the largest number of protruding fibers and was therefore the fuzziest. Sample 3 and Sample 11 had the smallest average fiber diameter. Sample 5 had a very closed surface and little internal void content. Thus, Sample 5 had low surface fuzz and very large fibers. Sample 3 was the thickest and had the largest internal void content. Sample 8 was the thinnest.

When Examples 13 and 14 were washed, the resulting non/woven fabric had the appearance and characteristics similar to the 60/40 PE/PEO blends and reactive blends of the preceding examples.

After producing the nonwoven fabric, several optional finishing steps may be carried out. For example, several plies of the fabric may be thermally bonded together between heated calendar rolls to form a multi-ply fabric, which wicks water better than a single ply fabric. Also, the strength of the fabric transverse to the machine direction can be increased by point bonding a single ply a spaced apart locations over the area of the fabric. Another option is to laminate the fabric to another type of film, foil, paper, woven or nonwoven fabric, or other substrate.

The present invention has been illustrated in great detail by the above specific examples. It is to be understood that these examples are illustrative embodiments and that this invention is not to be limited by any of the examples or details in the description. Those skilled in the art will recognize that the present invention is capable of many modifications and variations without departing from the scope of the invention. Accordingly, the detailed description and examples are meant to be illustrative and are not meant to limit in any manner the scope of the invention as set forth in the following claims. Rather, the claims appended hereto are to be construed broadly within the scope and spirit of the invention.

Now that the invention has been described,
What is claimed is:

1. A nonwoven fabric comprising primarily a water insoluble, grafted polyolefin including:
   at least one group of elongated fibers of said polyolefin substantially oriented along a longitudinal axis;
   a plurality of branches of said fibers extending across multiple fibers in said fabric;
   thermal bonds formed between adjacent fibers and between said branches and fibers crossed by said branches; and
   elongated channels extending generally parallel to said longitudinal axis on the surface of said fabric and within said fabric, a substantial proportion of said channels being interconnected to other channels,
   said fabric having enhanced fluid intake and wicking.

2. The nonwoven fabric of claim 1 wherein said fabric is permanently wettable.

3. The nonwoven fabric of claim 1 wherein said fabric is produced from a film.

4. The nonwoven fabric of claim 1 wherein said elongated fibers are of variable cross sectional shape and variable diameter.

5. The nonwoven fabric of claim 1 wherein said fabric is porous.

6. The nonwoven fabric of claim 5 wherein said fabric defines surface pores having an average open area in a range from about 5% to about 24%.

7. The nonwoven fabric of claim 6 wherein said fabric includes internal voids averaging in a range from about 3% to about 51% of the volume of said fabric.

8. The nonwoven fabric of claim 1 wherein said fabric includes internal voids averaging in a range from about 3% to about 51% of the volume of said fabric.

9. The nonwoven fabric of claim 5 wherein said fabric defines surface pores having an average equivalent hydraulic diameter in a range from about 1.5 micrometers to about 40 micrometers.

10. The nonwoven fabric of claim 5 wherein said fabric defines surface pores having an average equivalent circular diameter in a range from about 1.5 micrometers to about 160 micrometers.

11. The nonwoven fabric of claim 1 wherein said fibers are formed from a grafted polyethylene.

12. The nonwoven fabric of claim 1 wherein said fabric is water-weakenable such that said fabric loses rigidity during prolonged contact with water.

13. The nonwoven fabric of claim 1 wherein said polyolefins are grafted with a polar vinyl monomer.

14. The nonwoven fabric of claim 13 wherein said polar vinyl monomer is polyethylene glycol methacrylate.

15. A nonwoven fabric comprising:
   groups of elongated polyolefin fibers substantially oriented along a longitudinal axis, said fibers having branches extending therefrom and bonded therebetween; and
   elongated channels extending generally parallel to said longitudinal axis on the surface of said fabric and within said fabric, a substantial portion of said channels being interconnected to other channels,
   wherein said fabric is formed from a composition comprising a volumetric majority of said polyolefin.

16. The nonwoven fabric of claim 13 wherein said fabric is permanently wettable.

17. The nonwoven fabric of claim 15 wherein said bonds having been formed during extrusion to form said polyolefin fibers.

18. The nonwoven fabric of claim 15 wherein said fibers are thermally bonded.

19. The nonwoven fabric of claim 15 wherein said elongated fibers are of variable cross sectional shape and variable diameter.

20. The nonwoven fabric of claim 15 wherein said fabric is porous.

21. The nonwoven fabric of claim 15 wherein said polyolefin fibers are formed from polyethylene.

22. The nonwoven fabric of claim 15 wherein said fabric is water-weakenable such that said fabric loses rigidity during prolonged contact with water.

23. A personal hygiene article comprising:
   a nonwoven, porous fabric including elongated polyolefin fibers substantially oriented along a longitudinal axis, said fibers having branches extending therefrom and bonded therebetween; and
   elongated channels extending generally parallel to said longitudinal axis on the surface of said fabric and within said fabric, a substantial portion of said channels being interconnected to other channels.

24. The personal hygiene article of claim 23 wherein said fabric is permanently wettable.

25. The personal hygiene article of claim 23 wherein said elongated fibers are of variable cross sectional shape and variable diameter.

* * * * *